US009008392B1

(12) United States Patent
Bai et al.

(10) Patent No.: US 9,008,392 B1
(45) Date of Patent: Apr. 14, 2015

(54) SYSTEMS AND METHODS FOR VISUALIZING ELONGATED STRUCTURES AND DETECTING BRANCHES THEREIN

(71) Applicant: HeartFlow, Inc., Redwood City, CA (US)

(72) Inventors: Ying Bai, Belmont, CA (US); Jonathan Tang, Redwood City, CA (US); Razik Yousfi, Burlingame, CA (US)

(73) Assignee: HeartFlow, Inc., Redwood City, CA (US)

( * ) Notice: Subject to any disclaimer, the term of this patent is extended or adjusted under 35 U.S.C. 154(b) by 0 days.

(21) Appl. No.: 14/495,722

(22) Filed: Sep. 24, 2014

Related U.S. Application Data

(60) Provisional application No. 61/882,502, filed on Sep. 25, 2013.

(51) Int. Cl.
*G06K 9/00* (2006.01)
*G06K 9/52* (2006.01)
*A61B 6/03* (2006.01)
*A61B 5/055* (2006.01)
*A61B 6/00* (2006.01)
*G06T 7/00* (2006.01)

(52) U.S. Cl.
CPC . *G06K 9/52* (2013.01); *A61B 6/032* (2013.01); *A61B 6/037* (2013.01); *A61B 5/055* (2013.01); *A61B 6/504* (2013.01); *G06T 7/0012* (2013.01)

(58) Field of Classification Search
None
See application file for complete search history.

(56) References Cited

U.S. PATENT DOCUMENTS

| | | | | |
|---|---|---|---|---|
| 5,254,859 A * | 10/1993 | Carman et al. | | 250/559.25 |
| 2005/0110791 A1* | 5/2005 | Krishnamoorthy et al. | | 345/419 |
| 2005/0195189 A1* | 9/2005 | Raman et al. | | 345/424 |
| 2007/0041644 A1* | 2/2007 | Kim et al. | | 382/190 |
| 2008/0100621 A1* | 5/2008 | Aharon et al. | | 345/424 |
| 2008/0132774 A1* | 6/2008 | Milstein et al. | | 600/407 |
| 2008/0187199 A1* | 8/2008 | Gulsun et al. | | 382/131 |
| 2008/0260205 A1* | 10/2008 | Von Berg et al. | | 382/103 |
| 2008/0273777 A1* | 11/2008 | Luboz et al. | | 382/130 |
| 2010/0010623 A1* | 1/2010 | Lashinski et al. | | 623/1.24 |
| 2011/0054318 A1* | 3/2011 | Shin et al. | | 600/443 |
| 2012/0122052 A1* | 5/2012 | Hackel | | 433/29 |
| 2013/0216110 A1* | 8/2013 | Zheng et al. | | 382/128 |
| 2014/0270436 A1* | 9/2014 | Dascal et al. | | 382/130 |

OTHER PUBLICATIONS

Kanitsar, A. et al. "CPR-Curved Planar Reformation." IEEE Visualization 2002. (2001): 37-44.
Kokubun, H. et al. "Radial intensity projection for lumen: application to CT angiographic imaging." Proc. SPIE 6142, Medical Imaging 2006: Physics of Medical Imaging, 61424R (Mar. 3, 2006); doi:10.1117/12.651498.
Wallis JW, Miller TR, Lerner CA, Kleerup EC. "Three-dimensional display in nuclear medicine." IEEE Trans Med Imaging. 1989;8(4):297-30.

* cited by examiner

*Primary Examiner* — Chan Park
*Assistant Examiner* — Mia M Thomas
(74) *Attorney, Agent, or Firm* — Bookoff McAndrews, PLLC

(57) ABSTRACT

Various embodiments of the present disclosure relate generally to medical imaging and related methods. More specifically, particular embodiments of the present disclosure relate to systems and methods for visualizing elongated structures.

20 Claims, 11 Drawing Sheets

SYSTEMS AND METHODS FOR VISUALIZING ELONGATED STRUCTURES AND DETECTING BRANCHES THEREIN

RELATED APPLICATION

This application claims the benefit of priority from U.S. Provisional Application No. 61/882,502, filed on Sep. 25, 2013, which is herein incorporated by reference in its entirety.

TECHNICAL FIELD

Various embodiments of the present disclosure relate generally to medical imaging and related methods. More specifically, particular embodiments of the present disclosure relate to systems and methods for visualizing elongated structures.

BACKGROUND

An important topic in medical imaging is the visual representation of elongated structures, such as tubular branching structures, such as, for example, blood vessels, or airways in volumetric data sets. To identify these structures and visualize all branches from a primary centerline, many types of visualization methods have been utilized. However, such methods are limited in their ability to display the entirety of these structures "at a glance."

As an example, two popular reconstruction methods for the display of blood vessels and other branching structures are the curved planar reformation (CPR) view and the straightened curved planar reformation (sCPR) view. The CPR and sCPR views utilize the luminal centerline to calculate a two dimensional planar view projected along the centerline. Although a planar view displays the length of the entire vessel, these views may not provide sufficient information on the entire circumferential surface of the vessel at a glance. Thus, branching vessels that leave from the surface of the vessel may not be represented at all times in these views.

Another imaging technique used in medical imaging is a maximum intensity projection (MIP). An MIP view may display the projection of voxels with maximum intensity along parallel rays originating from the viewpoint to the plane of projection. This technique may display vessels of small caliber, since the maximum intensity along the ray is displayed and tortuous vessels may be visible in one view. However, any bright structures along the ray may obstruct the view, and may prevent the vessels from being visualized. Additionally, this technique may not display the entire circumferential surface of the vessel at a glance.

Thus, a need exists for systems and methods, which provide sufficient information on the entire circumferential surface of the vessel at a glance.

The foregoing general description and the following detailed description are exemplary and explanatory only and are not restrictive of the disclosure.

SUMMARY

According to certain aspects of the present disclosure, systems and methods are disclosed for visualizing structures. One such method may include: acquiring, using a processor, digital data of a portion of an elongate object; identifying, using a processor, a centerline connecting a plurality of points within the portion of the elongate object; defining a first half-plane along the centerline; traversing a predetermined angular distance in a clockwise or counter clockwise direction from the first half-plane to a second half-plane to define an angular wedge; calculating, using a processor, a view of the angular wedge between the first half-plane and the second half-plane; and generating an electronic view of the angular wedge.

In some aspects, the method may include one or more of the following: further comprising, repeating the steps of traversing and calculating for one or more additional angular wedges of the portion of the elongate object; further comprising, aligning views of two opposing angular wedges next to each other; wherein the portion of the elongate object is a tubular structure, and/or, wherein generating the half-plane comprises: defining an origin direction for each of the plurality of points of the centerline; calculating, using a processor, a plurality of vectors, each originating from one of the plurality of points toward the origin direction; and combining the plurality of vectors to generate the half-plane. Other aspects may include one or more of the following: wherein calculating the view in an angular direction for the angular wedge between the first half-plane and the second half-plane comprises: determining vectors along the first half-plane; determining voxels along each of the vectors along the first half-plane; generating maximum intensity projection (MIP) rays in an angular direction around the first half-plane toward a predetermined angular distance for each of the voxels; for each MIP ray, creating a set of voxels that intersect the ray computed in a predetermined angular increment, and computing a maximum intensity of the set of voxels; and projecting the computed maximum intensity on the first half-plane. Other aspects may include one or more of the following: wherein each of the angular wedges is the same size; wherein calculating the view of the angular wedge comprises: determining vectors along the first half-plane and corresponding voxels along each of the vectors; generating maximum intensity projection (MIP) rays in an angular direction around the first half-plane for each of the voxels; for each MIP ray, creating a set of voxels that intersect the ray computed in a predetermined angular increment, and computing the intensity of a maximum intensity voxel from the set of voxels, and projecting the computed maximum intensity on the first half-plane. Other aspects may include one or more of the following: wherein the elongate object comprises tubular branching structures; wherein the steps of traversing and calculating are repeated until a complete circumferential view of the portion of the elongate object is completed; further comprising assembling views of opposing angular wedges next to each other; wherein the digital image data is generated from computed tomography imaging; and/or wherein views of opposing angular wedges are displayed to resemble a straightened curved planar reformation view.

According to another aspects, disclosed is a system for visualizing structures which may include: a data storage device storing instructions for visualizing structures; and a processor configured to execute the instructions to perform a method including the steps of: acquiring, using a processor, digital data of a portion of an elongate object; identifying, using a processor, a centerline connecting a plurality of points within the portion of the elongate object; defining a first half-plane along the centerline; traversing a predetermined angular distance in a clockwise or counter clockwise direction from the first half-plane to a second half-plane to define an angular wedge; calculating, using a processor, a view of the angular wedge between the first half-plane and the second half-plane; and generating an electronic view of the angular wedge.

According to certain aspects, disclosed is a non-transitory computer readable medium for use on at least a computer system containing computer-executable programming instructions for visualizing structures, the instructions may be executable by the computer system for: acquiring, using a processor, digital data of a portion of an elongate object; identifying, using a processor, a centerline connecting a plurality of points within the portion of the elongate object; defining a first half-plane along the centerline; traversing a predetermined angular distance in a clockwise or counter clockwise direction from the first half-plane to a second half-plane to define an angular wedge; calculating, using a processor, a view of the angular wedge between the first half-plane and the second half-plane; and generating an electronic view of the angular wedge.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

As described above, a visual representation of tubular structures in general, and tubular branching structures, such as blood vessels, airways, etc., is an important tool for diagnosing the health of patients. Current visualization techniques provide limited views of tubular structures. The present disclosure is directed to a new approach for providing visualization of tubular structures that may display the entire circumferential surface of a tubular structure. More specifically, the present disclosure is directed to using patients' imaging of a tubular structure to generate a series of maximum intensity projection views of segments of the tubular structure and assembling the views to provide a complete circumferential visualization of the tubular structure. Such views may be used to generate patient-specific models of flow within the tubular structure, predict medical events (e.g. cardiac, pulmonary, respiratory), including plaque rupture and/or myocardial infarction. The visualization methods and systems of the present disclosure may be used to generate a physics-based simulation of flow through the tubular structure (e.g. blood flow and airflow) to predict those medical events. In addition, the present disclosure includes the use of machine learning or rule-based methods to achieve the predictions. Furthermore, the machine-learning and rule-based methods may incorporate various risk factors, including patient demographics, biomarkers, and/or coronary geometry, as well as the results of patient-specific biophysical simulations (e.g., hemodynamic characteristics). If additional diagnostic test results are available, those results can be used to train a machine-learning algorithm, for example, in making a prediction.

Figure 1:
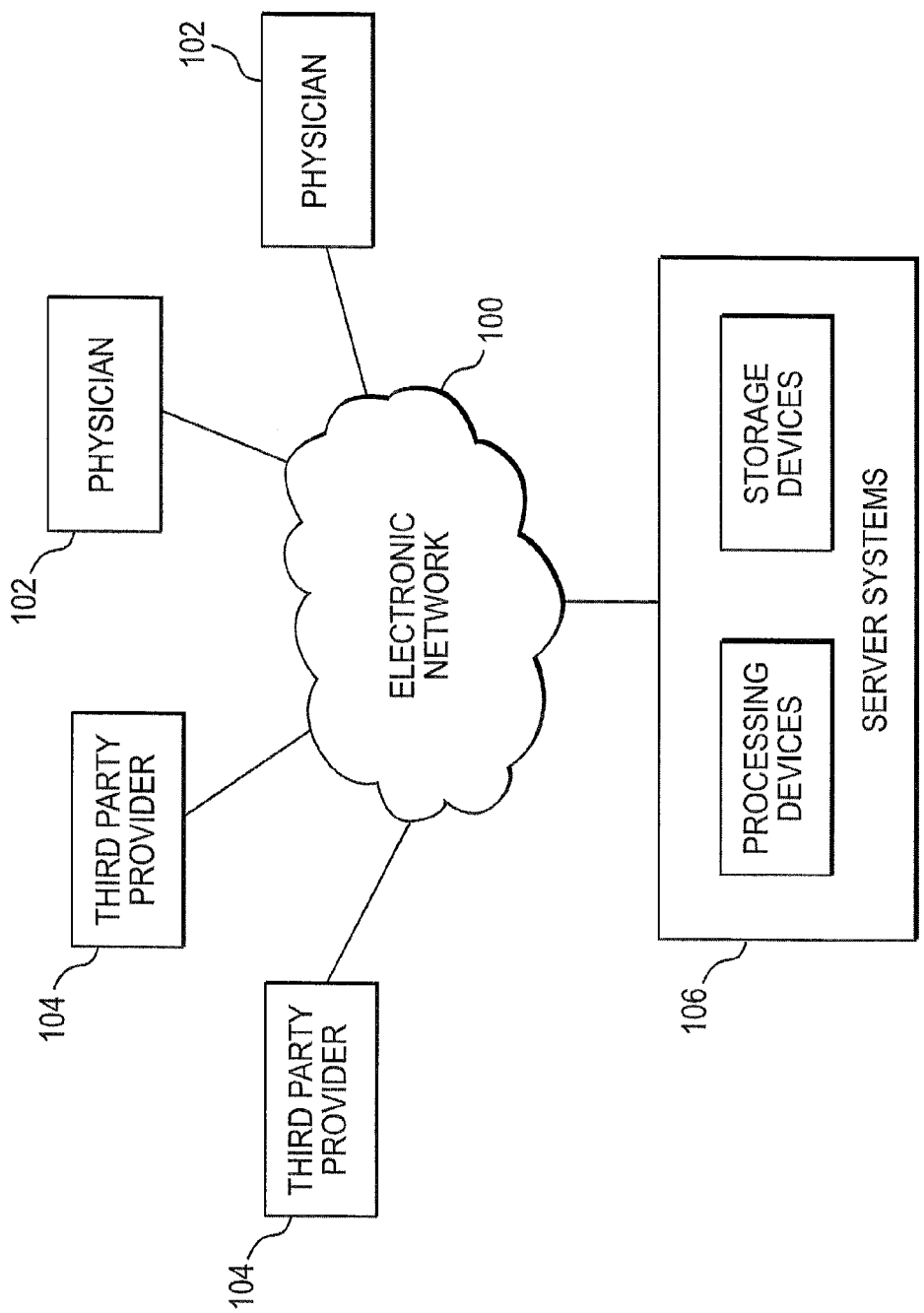
FIG. 1 is a block diagram of an exemplary system and network for providing visualization of elongated structures, according to an exemplary embodiment of the present disclosure.

Referring now to the figures, FIG. 1 depicts a block diagram of an exemplary system and network for predicting coronary plaque vulnerability from patient-specific anatomic image data. Specifically, FIG. 1 depicts a plurality of physicians 102 and third party providers 104, any of whom may be connected via wired and/or wireless connections to an electronic network 100, such as the Internet, through one or more computers, servers, and/or handheld mobile devices. Physicians 102 and/or third party providers 104 may create or otherwise obtain images of one or more patients' cardiac and/or vascular systems. The physicians 102 and/or third party providers 104 may also obtain any combination of patient-specific information, such as age, medical history, blood pressure, blood viscosity, etc. Physicians 102 and/or third party providers 104 may transmit the cardiac/vascular images and/or patient-specific information to server systems 106 over the electronic network 100 via electronic devices. The information may be transmitted in any suitable manner, for example, the information may be encrypted, encoded, compressed, or otherwise digitally modified, and the server systems 106 may decode, decrypt, decompress, or otherwise process the information received. Server systems 106 may include storage devices for storing images and data received from physicians 102 and/or third party providers 104. Server systems 106 may also include processing devices for processing images and data stored in the storage devices and may transmit, in an electronically secure manner, the processed images (e.g. the entire circumferential surface of a vessel) for display on electronic devices in a single display or view.

Figure 2A:
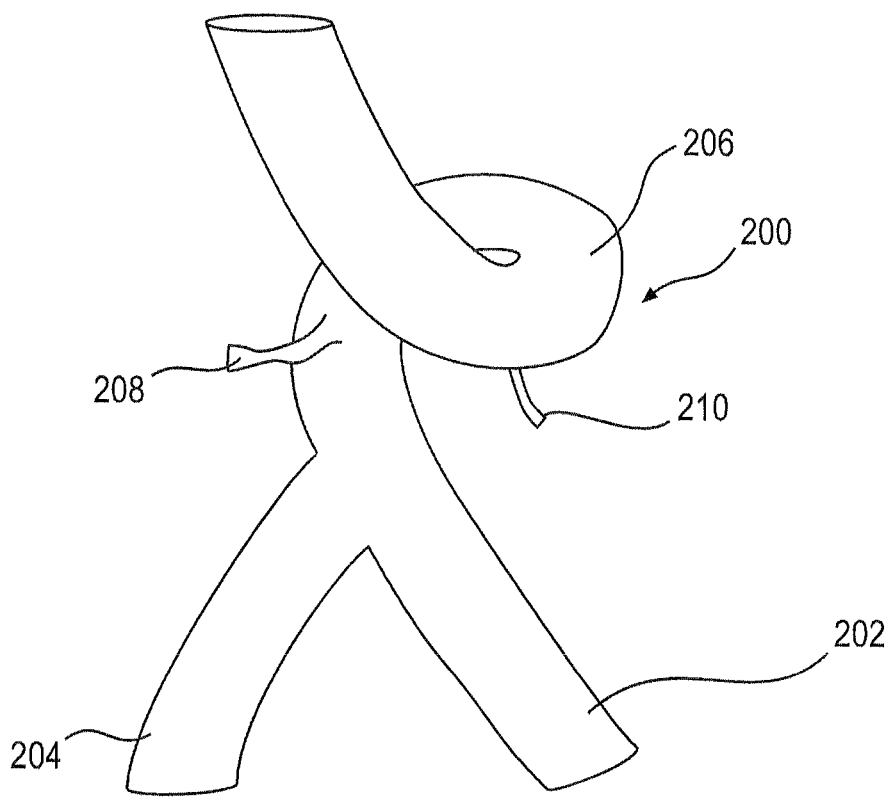
FIG. 2A is a tubular structure with branching structures for visualization, according to an exemplary embodiment of the present disclosure.

FIG. 2A is a tubular structure 200 with branching structures to be visualized, according to an exemplary embodiment of the present disclosure. The tubular structure 200 may be a vessel for fluid and/or airflow and may be located in any organ of the body such as the heart or lungs. In one example, the tubular structure may be all or a portion of a blood vessel. The tubular structure 200 may have any diameter and thickness and may have one or more curved portions. The tubular structure 200 may include one or more branches 202 and 204 and one or more tortuous portions 206. In addition, the tubular structure may include smaller tubular branches 208 and 210. The tubular structure 200 may have any size and shape and may include one or more anatomical features, such as valves, clots, plaque, and/or lesions.

Figure 3:
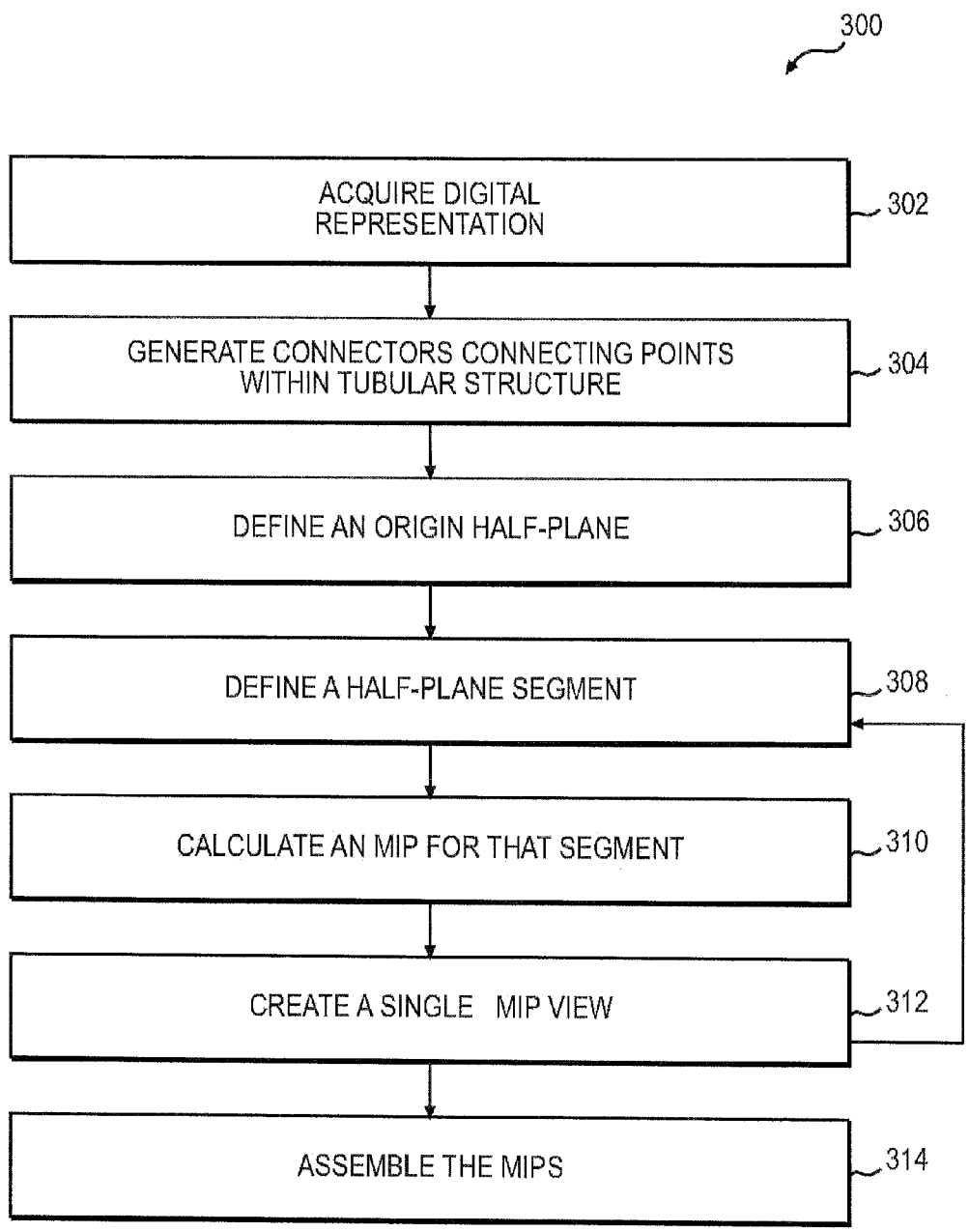
FIG. 3 is a block diagram of an exemplary method for performing visualization of a tubular structure, according to an exemplary embodiment of the present disclosure.

FIG. 3 is a block diagram of an exemplary method 300 for providing visualization of a tubular structure, according to an exemplary embodiment of the present disclosure. The method 300 may be performed by server systems 106, based on information, images, and data received from physicians 102 and/or third party providers 104 over an electronic network 100. The method of 300 may include acquiring a digital representation of patient image data at step 302. The patient image data may be data from one or more imaging sources such as tomography (e.g. computed tomography (CT), computed tomography angiography (CCTA), singe-photon emission computed tomography (SPECT), magnetic resonance imaging (MRI), positron emission tomography (PET), electron tomography, ultrasound, etc. The patient image data may be of one or more portions of a patient, such as an image of a tubular structure, such as tubular structure 200. For example, a CCTA scan of a patient may be performed to acquire an image of the patient's vessels of interest including the ascending aorta, and the left/right coronary artery trees. A digital representation of the patient image data may be stored in electronic memory, such as on a hard drive, network drive, removable memory, etc. accessible by a computational device such as a computer, laptop, DSP, server, tablet, mobile device, etc.

Figure 2B:
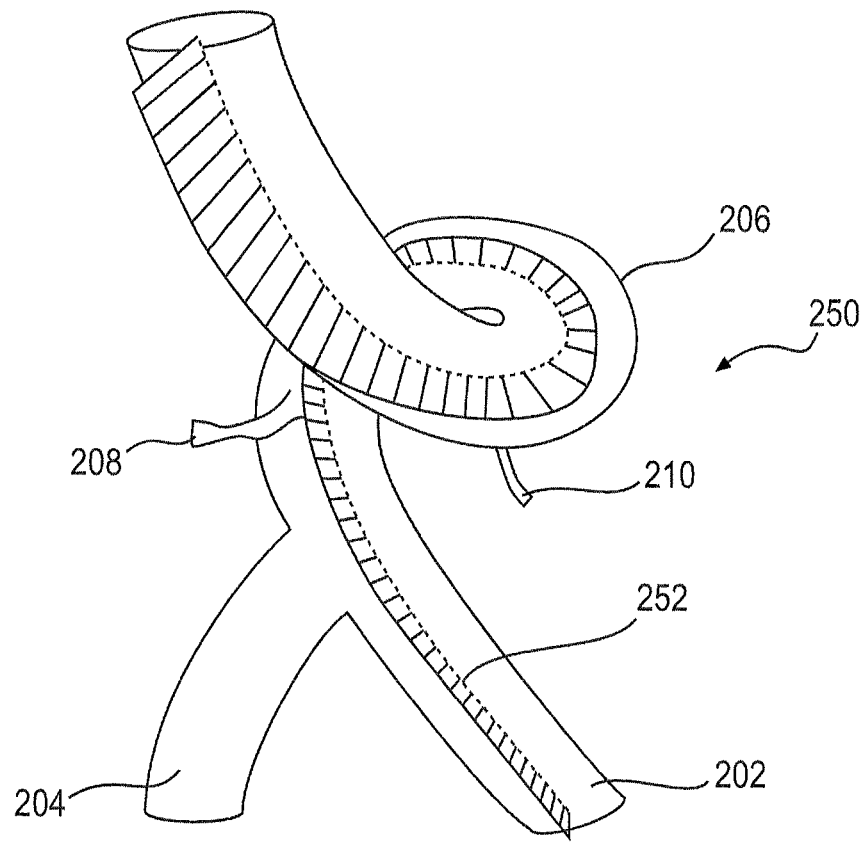
FIG. 2B is the tubular structure of FIG. 2A with an arbitrarily defined 0° half-plane along a portion of the tubular structure, according to an exemplary embodiment of the present disclosure.

A patient specific model may be derived from the patient image data in any suitable manner, for example, by generating one or more connectors connecting points within tubular structures at step 304. One of the connectors may be defined as the centerline of the tubular structure. An example of a centerline 252 of the tubular structure 200 is shown in FIG. 2B. The centerline 252 may be one of a number of manually or automatically electronically generated centerlines that connect points with the tubular structure 200 and may be electronically stored.

The connectors may be generated in any suitable manner, for example from a CCTA scan that is automatic, semi-automatic, or manual. The connectors may include the connected points along the tubular structure. The centerline may identify a tubular structure of interest, such as a blood vessel, and may have one or more branches from the tubular structure.

Figure 4:
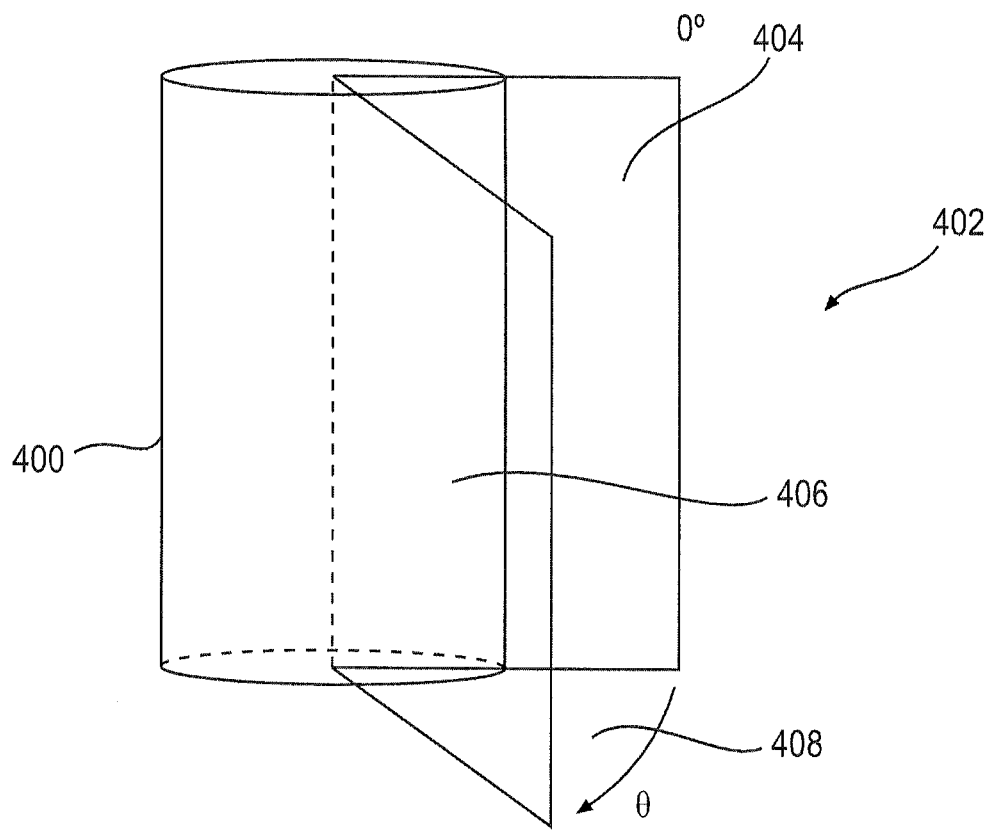
FIG. 4 is a side view of a tubular structure with wedge-like shape between two half-planes, according to an exemplary embodiment of the present disclosure.

An origin half-plane may be defined at step 306 for the centerline of the tubular structure defined in 304. The origin half-plane may be generated by defining a zero degree direction for each point in the centerline. A vector may then be calculated originating from the centerline point and extending in the zero degree direction. Each vector from each point in the centerline may be combined to create a half-plane at zero degrees. An example of an origin half plane 402 of a tubular structure 400 is shown in FIG. 4. As shown in FIG. 4, the origin half plane 402 may comprise half planes 404 and 406 defining a wedge shaped segment (a wedge) having an angle 408.

A half-plane segment may be defined at step 308 by using the zero degree direction (half-plane) as a starting point and defining a predetermined angular distance from the zero degree vector. The predetermined angular distance may be any suitable distance determined by the manufacturer of the system or inputted by the user. For example, the predetermined angular distance may be 15 degrees, 30 degrees, 60 degrees, 90 degrees, etc. The direction of the predetermined angular distance from the zero degree vector may be clockwise or counterclockwise around the centerline point. For each vector defined in step 306, the predetermined angular distance from the origin vector may be calculated. For example, for each vector defined in step 306, a vector 60 degrees from the origin vector in a clockwise direction around the centerline point may be calculated. Each vector along the center line may be combined to create a half-plane at the predetermined angular distance.

Figure 5:
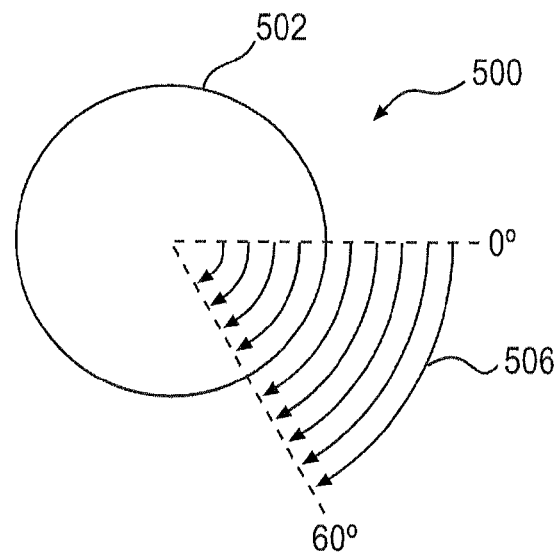
FIG. 5 is an axial cross-sectional view of the tubular structure of FIG. 4 with arrows indicating a direction of maximum intensity projection (MIP) rays.

A MIP may be calculated at step 310. The MIP may be calculated in an angular direction between the zero degree half-plane and the predetermined angular distance. An example of MIP rays is shown in FIG. 5, which shows an axial (cross-sectional) view 500 of a tubular structure 502 with arrows indicating the direction of MIP rays 506. For example:

for all 0° vectors along the centerline:
1. Cast maximum intensity projection (MIP) rays in the angular direction around the centerline towards the 60° half-plane.
2. For each MIP ray:
   a. Create a set of voxels that the ray intersects, computed in 1° increments.
   b. Compute the maximum intensity of the set of voxels from the previous step.
3. Project the voxel with maximum intensity to the originating voxel on the 0° vector. For example, the value of the voxel with the maximum intensity may be assigned to the originating voxel of the 0° vector.

Figure 8:
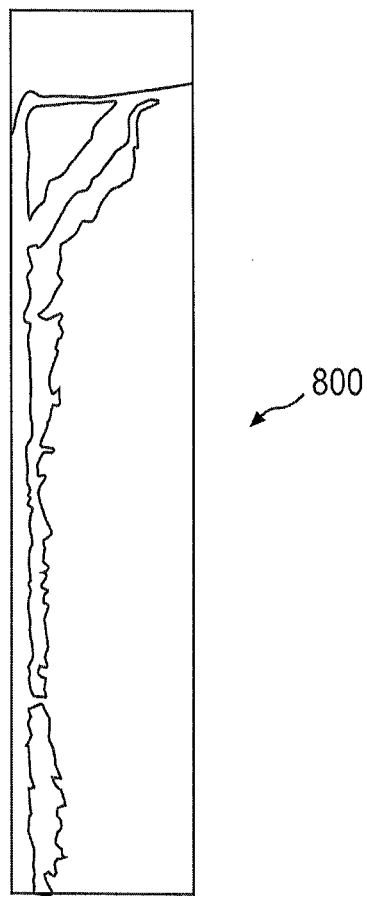
FIG. 8 is a single MIP in an angular direction (aMIP) view of a tubular structure, according to an exemplary embodiment of the present disclosure.

The steps of computing a MIP in the angular direction (an aMIP), for example, as described above, may be performed on a graphics-processing unit (GPU) of the computational device for improved efficiency. The computation of the maximum intensity may occur sequentially as described in the above example, or in any order. For example, the computation of the maximum intensity may be performed for any order of vectors and voxels for improved efficiency. An example of a single aMIP is shown in FIG. 8, view 800.

Figure 6:
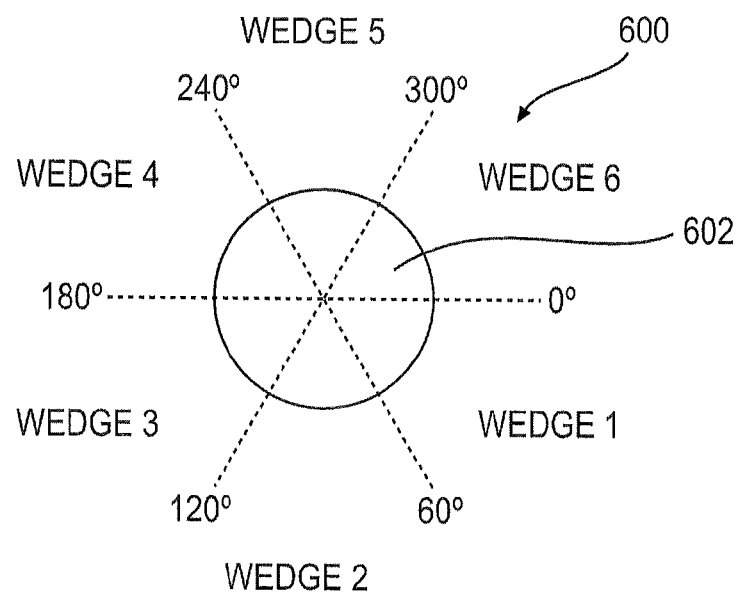
FIG. 6 is an axial cross-sectional view showing division of the tubular structure of FIG. 4 into wedge sections, according to an exemplary embodiment of the present disclosure.

The steps of defining a half-plane segment 308 and calculating an aMIP for the wedge at step 310 may be repeated for each wedge having the predetermined angular distance until a full 360 degree circumferential MIP view is obtained at step 312. For example, if the predetermined angular distance is 60 degrees, step 308 and 310 may be repeated for each 60 degree wedge (six times) for a total of six aMIP views. In this example, the wedges 602 may be constructed for the following set of half-planes 600 as shown in FIG. 6:

ii. 0°-60°
 iii. 60°-120°
 iv. 120°-180°
 v. 180°-240°
 vi. 240°-300°
 vii. 300°-360° (0°)

In some aspects, multiple wedges 602 may be computed simultaneously for improved efficiency. In some aspects, computation of an aMIP may be optimized by using full planes, in order to generate in a single pass a wedge and its opposite wedge (e.g. 0-60 and 180-240). In such an example, three full planes may be assembled instead of six half-plane to resemble three sCPR views placed side-by-side.

Figure 7:
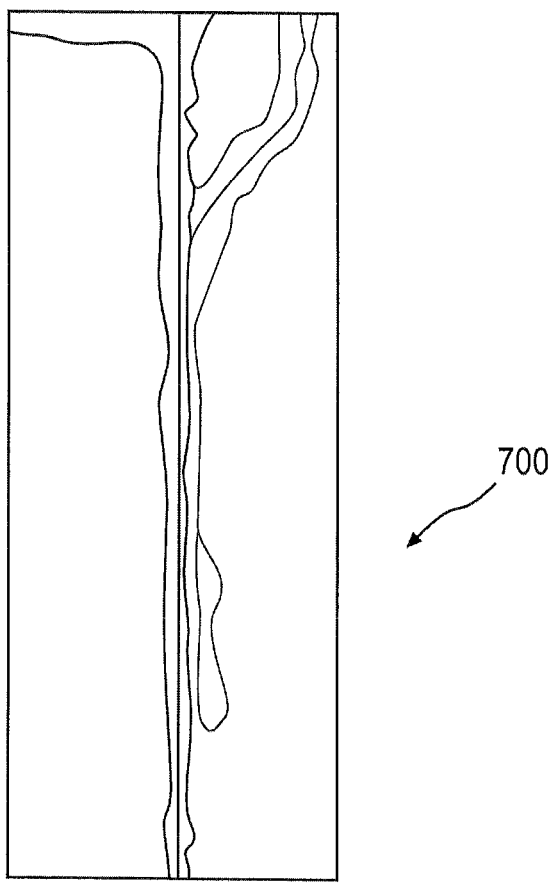
FIG. 7 is an example of a straightened curved planar reformation (sCPR) view of a portion of a tubular structure, according to an exemplary embodiment of the present disclosure.
Figure 9:
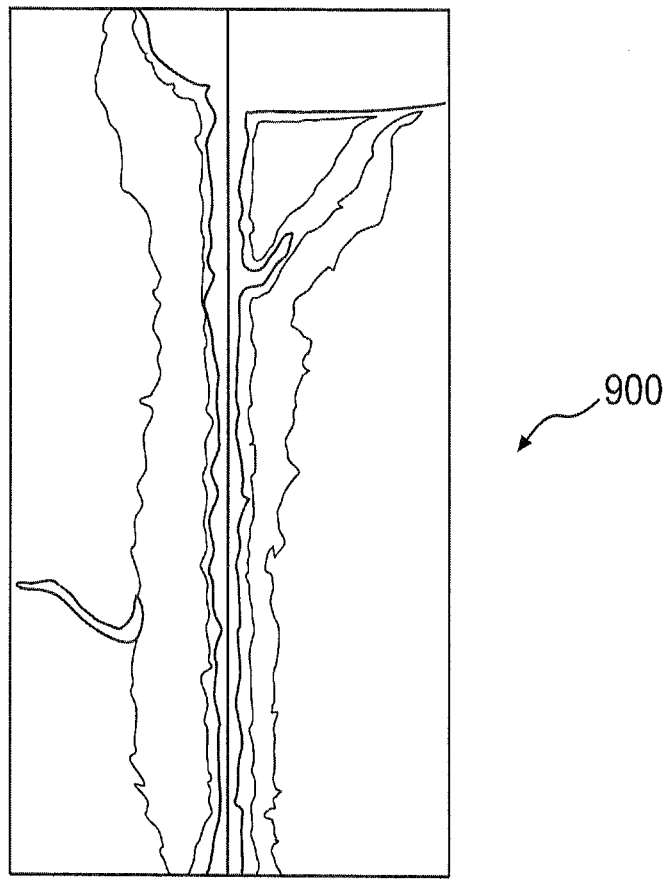
FIG. 9 is a dual aMIP view of a tubular structure, arranged to resemble an sCPR view as shown in FIG. 7, according to an exemplary embodiment of the present disclosure.
Figure 10:
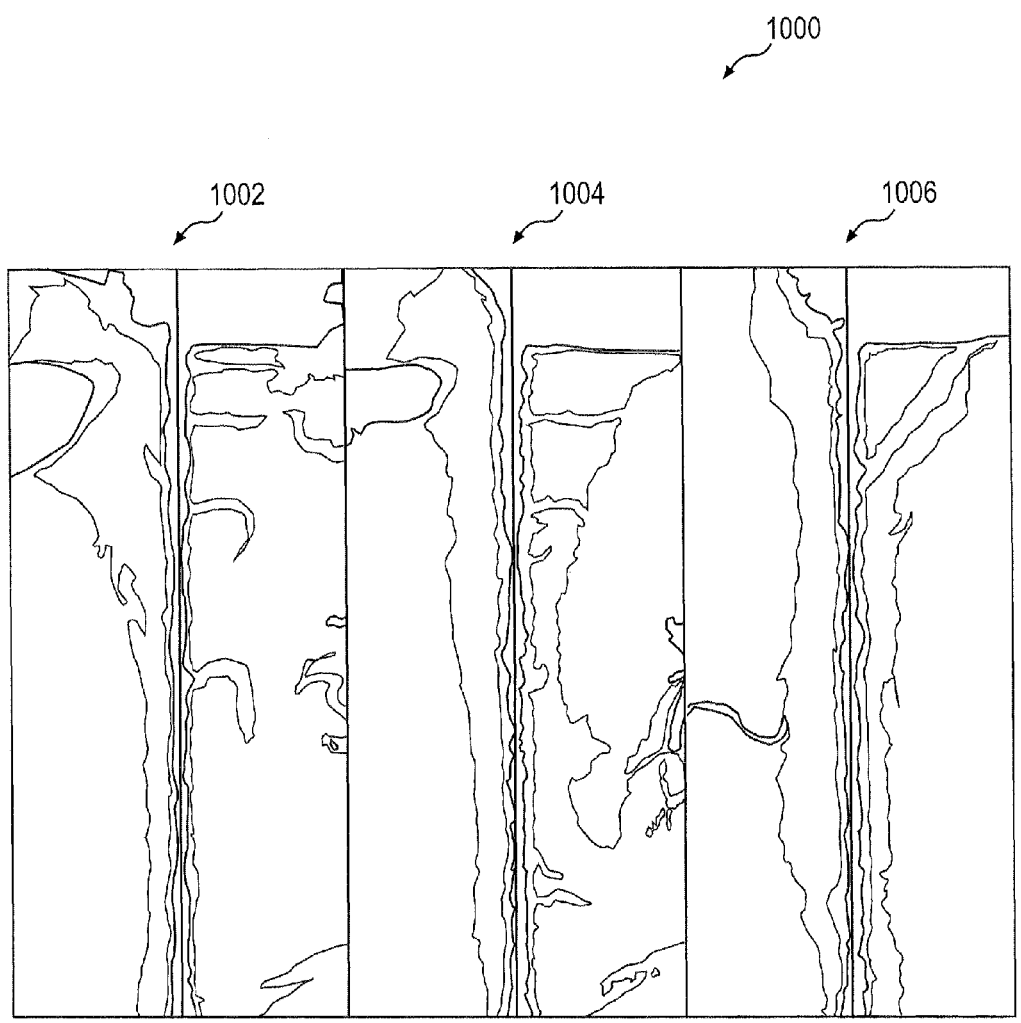
FIG. 10 is a view of six aMIPs of a tubular structure arranged to resemble three sCPR views, according to an exemplary embodiment of the present disclosure.

Each of the aMIP views may be assembled at step 314. As described above, an sCPR view, such as 700 of FIG. 7, may advantageously depict an entire vessel planar cross-section. However, such an sCPR may provide insufficient circumferential information, such as of branching structures. As a results, the aMIP views may be assembled on a display for viewing in any suitable manner to resemble three sCPR views placed side-by-side. For example:

a. For the 180°-240° aMIP, the 240°-300° aMIP, and the 300°-360° (0°) aMIP, reflect the views across the centerline. For example, for each 0° vector along the centerline, the values of the voxels in the opposite direction may be re-ordered to create an inverted view.

b. Align the origin of the centerlines in the same direction.

c. Align the centerline of the 0°-60° aMIP and the reflected 180°-240° aMIP to create an image comprising two aligned aMIP views 900 as shown in FIG. 9, to resemble the first sCPR view 700 shown in FIG. 7.

d. Aligning the centerline of the 60°-120° aMIP and the reflected 240°-300° aMIP to create an image resembling a second sCPR view.

e. Aligning the centerline of the 120°-180° aMIP and the reflected 300°-360° (0° aMIP to create an image resembling a third sCPR view.

f. Aligning an edge of the combined aMIP views from step (c) with an edge of the combined aMIP views from step (d) to create an image of four aMIP views resembling two sCPR views.

g. Aligning an edge of the combined aMIP views from step (f) which form an image resembling two sCPR views with an edge of the third sCPR view from step (e) to create an image of six aMIP views resembling three sCPR views 1002, 1004, and 1006, as shown in FIG. 10, view 1000.

h. Three planes may be used to simultaneously calculate and display the views for improved efficiency, for example, in the following manner:
   i. When calculating the 0° vector, use the opposite direction for the 180° vector.
   ii. Combining the above to create a line. This line, when combined with all lines for the centerline, may define the 0° plane
   iii. Computing the 0°-60° aMIP and the 180°-240° aMIP views simultaneously by using the line rather than the vector for all centerline points to obtain a set of aMIP views identical to the one calculated in step c.

The three sets of aMIP views in steps (c)-(e) may be calculated simultaneously by using the method described in steps (h)(i) thru (h)(iii) for improved efficiency. Embodiments of the present disclosure may apply the MIP technique in an angular direction and may use multiple aMIPs in combination.

Using the above-disclosed technique, the entire centerline path may be visualized and the entire circumferential surface of a vessel may be displayed using a set of static views in one display.

Figure 11:
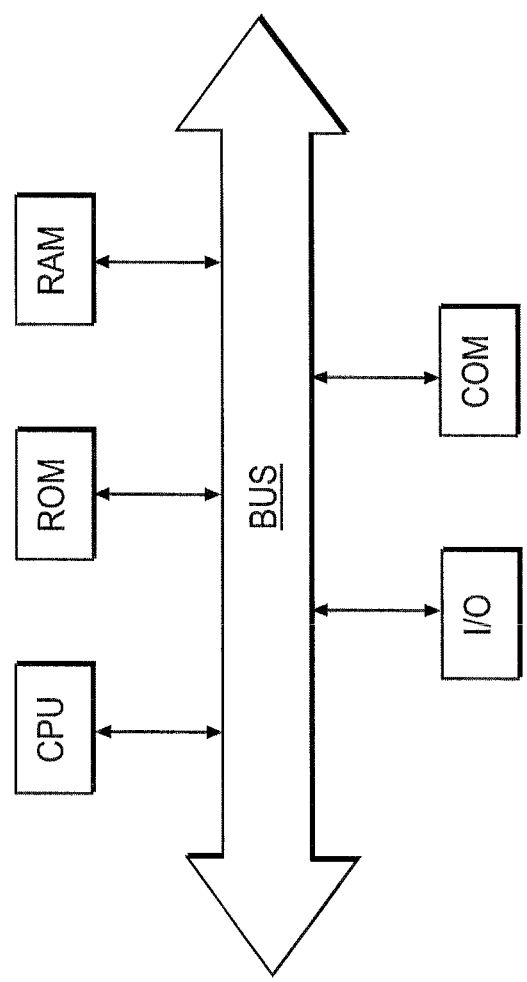
FIG. 11 is a simplified block diagram of an exemplary computer system in which embodiments of the present disclosure may be implemented.

FIG. 11 provides a functional block diagram illustration of general purpose computer hardware platforms. FIG. 11 illustrates a network or host computer platform as may typically be used to implement a server, such as user server systems 106 and/or any other server executing a visualization method such as method 300. It is believed that those skilled in the art are familiar with the structure, programming, and general operation of such computer equipment and as a result, the drawings should be self-explanatory.

A platform for a server or the like may include a data communication interface for packet data communication. The platform may also include a central processing unit (CPU) in the form of one or more processors, for executing program instructions. The platform typically includes an internal communication bus program storage and data storage for various data files to be processed and/or communicated by the platform such as ROM and RAM, although the server often receives programming and data via network communications. The hardware elements, operating systems, and programming languages of such equipment are conventional in nature, and it is presumed that those skilled in the art are adequately familiar therewith. The server also may include input and output ports to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

The many features and advantages of the disclosure are apparent from the detailed specification, and thus, it is intended by the appended claims to cover all such features and advantages of the disclosure which fall within the true spirit and scope of the disclosure. Further, since numerous modifications and variations will readily occur to those skilled in the art, it is not desired to limit the disclosure to the exact construction and operation illustrated and described, and accordingly, all suitable modifications and equivalents may be resorted to, falling within the scope of the disclosure.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed:

1. A computer-implemented method for visualizing elongate objects, the method comprising:
    acquiring, using a processor, digital data of a portion of an elongate object, the digital data being generated by a medical imaging device imaging a portion of a patient's body;
    identifying, using a processor, a centerline connecting a plurality of points within the portion of the elongate object;
    defining a first half-plane along the centerline, the first half-plane defining a planar area extending radially outward from the centerline along at least an axial distance of the elongate object;
    defining an angular wedge of the elongate object by traversing a predetermined angular distance in a clockwise or counter clockwise direction from the first half-plane to a second half-plane extending radially outward from the centerline at the predetermined angular distance from the first half-plane along at least the axial distance of the elongate object;
    calculating, using a processor, a view of the angular wedge between the first half-plane and the second half-plane; and
    generating an electronic view of the angular wedge.

2. The method of claim 1, further comprising, repeating the steps of traversing and calculating for one or more additional angular wedges of the portion of the elongate object.

3. The method of claim 2, further comprising, aligning views of two opposing angular wedges next to each other.

4. The method of claim 1, wherein generating the half-plane comprises:
    defining an origin direction for each of the plurality of points of the centerline;
    calculating, using a processor, a plurality of vectors, each originating from one of the plurality of points toward the origin direction; and
    combining the plurality of vectors to generate the half-plane.

5. The method of claim 1, wherein calculating the view of the angular wedge between the first half-plane and the second half-plane comprises:
    determining vectors along the first half-plane;
    determining voxels along each of the vectors along the first half-plane;
    generating maximum intensity projection (MIP) rays in an angular direction around the first half-plane toward a predetermined angular distance for each of the voxels;
    for each MIP ray, creating a set of voxels that intersect the ray computed in a predetermined angular increment, and computing a maximum intensity of the set of voxels; and
    projecting the computed maximum intensity on the first half-plane.

6. The method of claim 1, wherein calculating the view of the angular wedge comprises:
    determining vectors along the first half-plane and corresponding voxels along each of the vectors;
    generating maximum intensity projection (MIP) rays in an angular direction around the first half-plane for each of the voxels;
    for each MIP ray, creating a set of voxels that intersect the ray computed in a predetermined angular increment, and computing the intensity of a maximum intensity voxel from the set of voxels, and
    projecting the computed maximum intensity on the first half-plane.

7. The method of claim 1, wherein the elongate object comprises tubular branching structures.

8. The method of claim 1, wherein the steps of traversing and calculating are repeated for a plurality of angular wedges until a complete circumferential view of the portion of the elongate object is completed.

9. The method of claim 8, further comprising assembling views of opposing angular wedges next to each other.

10. The method of claim 9, wherein the views of the opposing angular wedges are displayed to resemble a straightened curved planar reformation view.

11. The method of claim 1, wherein the digital image data is generated from computed tomography imaging.

12. A system for visualizing structures comprising, the system comprising: a data storage device storing instructions for visualizing structures; and
    a processor configured to execute the instructions to perform a method including the steps of:
    acquiring, using a processor, digital data of a portion of an elongate object, the digital data being generated by a medical imaging device imaging a portion of a patient's body;
    identifying, using a processor, a centerline connecting a plurality of points within the portion of the elongate object;
    defining a first half-plane along the centerline, the first half-plane defining a planar area extending radially outward from the centerline along at least an axial distance of the elongate object;
    defining an angular wedge of the elongate object by traversing a predetermined angular distance in a clockwise or counter clockwise direction from the first half-plane to a second half-plane extending radially outward from the centerline at the predetermined angular distance from the first half-plane along at least the axial distance of the elongate object;
    calculating, using a processor, a view of the angular wedge between the first half-plane and the second half-plane; and generating an electronic view of the angular wedge.

13. The system of claim 12, further comprising, repeating the steps of traversing and calculating for one or more additional angular wedges of the portion of the elongate object.

14. The system of claim 13, further comprising, aligning views of two opposing angular wedges next to each other.

15. The system of claim 12, wherein generating the one or more centerlines comprises:
    defining an origin direction for each of the plurality of points of the centerline;
    calculating, using a processor, a plurality of vectors, each originating from one of the plurality of points toward the origin direction; and
    combining the plurality of vectors to generate the half-plane.

16. The system of claim 12, wherein calculating the view of the angular wedge between the first half-plane and the second half-plane comprises:
    determining vectors along the first half-plane;
    determining voxels along each of the vectors along the first half-plane;
    generating maximum intensity projection (MIP) rays in an angular direction around the first half-plane toward a predetermined angular distance for each of the voxels;
    for each MIP ray, creating a set of voxels that intersect the ray computed in a predetermined angular increment, and computing a maximum intensity of the set of voxels; and
    projecting the computed maximum intensity on the first half-plane.

17. The system of claim 12, wherein calculating the view of the angular wedge comprises:
- determining vectors along the first half-plane and corresponding voxels along each of the vectors;
- generating maximum intensity projection (MIP) rays in an angular direction around the first half-plane for each of the voxels;
- for each MIP ray, creating a set of voxels that intersect the ray computed in a predetermined angular increment, and
- computing the intensity of a maximum intensity voxel from the set of voxels, and
- projecting the computed maximum intensity on the first half-plane.

18. The system of claim 12, wherein the calculating step is performed by a graphics processing unit.

19. The system of claim 12, wherein the elongate object comprises tubular branching structures.

20. A non-transitory computer readable medium for use on at least a computer system containing computer-executable programming instructions for visualizing structures, the instructions being executable by the computer system for:
- acquiring, using a processor, digital data of a portion of an elongate object, the digital data being generated by a medical imaging device imaging a portion of a patient's body;
- identifying, using a processor, a centerline connecting a plurality of points within the portion of the elongate object;
- defining a first half-plane along the centerline, the first half-plane defining a planar area extending radially outward from the centerline along at least an axial distance of the elongate object; defining an angular wedge of the elongate object by traversing a predetermined angular distance in a clockwise or counter clockwise direction from the first half-plane to a second half-plane extending radially outward from the centerline at the predetermined angular distance from the first half-plane along at least the axial distance of the elongate object;
- calculating, using a processor, a view of the angular wedge between the first half-plane and the second half-plane; and
- generating an electronic view of the angular wedge.

* * * * *